United States Patent

Szekely et al.

[11] Patent Number: 5,912,267
[45] Date of Patent: Jun. 15, 1999

[54] PESTICIDE FORMULATIONS AND PROCESS FOR THE MANUFACTURE THEREOF

[75] Inventors: Istvan Szekely, Dunakeszi; Sandor Botar, Budapest; Bela Bertok, Budapest; Janis Hajimichael, Budapest; Jeno Kiraly, Budapest; Janosne Hadobas, Budapest; Laszlo Pap, Budapest; B. Iidiko Menesine, Veszprem, all of Hungary

[73] Assignee: Chinoin Pharmaceutical & Chemical Works Co., Ltd., Budapest, Hungary

[21] Appl. No.: 08/945,353

[22] PCT Filed: Apr. 19, 1996

[86] PCT No.: PCT/HU96/00020

§ 371 Date: Dec. 23, 1997

§ 102(e) Date: Dec. 23, 1997

[87] PCT Pub. No.: WO96/33615

PCT Pub. Date: Oct. 31, 1996

[30] Foreign Application Priority Data

Apr. 24, 1995 [HU] Hungary ................... 9501147

[51] Int. Cl.⁶ .................. A01N 53/00; A01N 53/14; A01N 25/04; A01N 25/30
[52] U.S. Cl. .............. 514/521; 514/531; 514/770; 514/772; 514/937; 514/941; 514/949; 514/970; 424/405
[58] Field of Search ............... 514/521, 531, 514/770, 772, 937, 941, 949, 970; 424/405

[56] References Cited

U.S. PATENT DOCUMENTS

| 4,607,050 | 8/1986 | Kieran et al. | 514/520 |
|---|---|---|---|
| 4,997,642 | 3/1991 | Curtis et al. | 514/521 |
| 5,153,349 | 10/1992 | Zoltan et al. | 558/354 |
| 5,192,793 | 3/1993 | Székely et al. | 514/421 |

FOREIGN PATENT DOCUMENTS

| 0029626 | 6/1981 | European Pat. Off. . |
| 0208758 | 1/1987 | European Pat. Off. . |
| 2251621 | 7/1992 | United Kingdom . |

OTHER PUBLICATIONS

*The Pesticide Manual*, 9th Edition, pp. 212–213 (No Date Available).

Gubelmann–Bonneau, I. et al., Tristyrylphenol Surfactants in Agricultural Formulations: Properties and Challenges in Applications, ASTM, SuperTech. Publ. (Pestic. Formulations and Applied Systems, 14th Col., pp. 119–136 (1995).

Derwent Abstract Accession No. 76–02668 (1976), Abstracting JP 50–83268 (Jul. 5, 1975).

*Primary Examiner*—John Pak
*Attorney, Agent, or Firm*—Birch, Stewart, Kolasch & Birch, LLP

[57] ABSTRACT

The subject of the invention is an aqueous suspension containing: 0.1–20% by mass beta-cypermethrin, 0–40% by mass other pesticide substance, 1–10% by mass surface active substances in total and within this, 1–5% by mass ethoxylated polyaryl-phenol-phosphate or sulfate, 0.1–25% by mass mineral and/or synthetic silicates, 0.1–1% by mass synthetic silicic acid and up to 100% by mass other auxiliary materials and water as dispersant.

15 Claims, No Drawings

PESTICIDE FORMULATIONS AND PROCESS FOR THE MANUFACTURE THEREOF

This application is a 371 of PCT/HU96/00020, filed on Apr. 19, 1996.

The invention relates to pesticide aqueous suspensions containing beta-cypermethrin as insecticide active ingredient in 0.1 to 20% by mass beside physical and chemical stabilizers. Further subject of the invention is a process for the preparation of these suspensions.

Beta-cypermethrin (The Pesticide Manual 9th Edition p 212–213) is approximately a 2:3 mixture of the following enantiomer pairs: (S)-α-cyano-3-phenoxy/benzyl-(1R)-cis-3-(2,2-dichlorovinyl)-2,2-dimethyl/cyclopropane/carboxylate and (R)-α-cyano-3-phenoxy/benzyl-(1S)-cis-3-(2.2-dichlorovinyl)-2,2-dimethyl/cyclopropane/carboxylate with (S)-α-cyano-3-phenoxyvbenzyl-(1R)-trans-3-(2,2-dichlorovinyl)-2,2-dimethyl/cyclopropane/carboxylate and (R)-α-cyano-3-phenoxy/benzyl-(1S)-trans-3-(2,2-dichlorovinyl)-2,2-dimethyl/cyclopropane/carboxylate in the form of trielin cristalls. It is a well known very effective insecticide introduced to the market by CHINOIN Pharmaceutical and Chemical Works Co. Ltd. in 1989 under the name of CHINMIX. Beta-cypermethrin, its synthesis and compositions containing beta-cypermethrin as active ingredient are described in Hungarian patent specification Nr. 198.612. European patent specification Nr. 0208758, USA Pat. specifications Nos. 5,192,739 and 5,153,349 and in the British patent specification Nr. 2,251,621.

The above mentioned patents describe procedures for the formulation of beta-cypermethrin where the active ingredient is dissolved in organic solvent(s), preferably in the presence or without the presence of emulsifiers. The product thus obtained will be sprayed out preferably emulsified in water. The manufactured and marketed preparations are all organic solutions of the active ingredient (Chinmix 5 EC, Chinmix ME, Cyperyl-S ULV).

Such preparations have beside their indisputable advantages (simple manufacturing, good stability and easy handling) several disadvantageous characteristics resulting mainly from the use of organic solvents. These are: fire and explosion danger, high toxicity, expensive packaging.

All these disadvantages can be eliminated if the active ingredient is formulated in an aqueous suspension. This way the easy handling and by using the appropriate formulation technology the biological effectiveness of the product equivalent to that of the solvent formulations can be preserved.

In aqueous suspension concentrates (known in plant protection as FW or SC formulations) the active ingredient is present in a fine (usually in a few $\mu$m size) colloidal state. Physical stability of the system is ensured by surface active substances, antifreeze substances, thickeners and other auxiliaries substances. The extremely low particle size is achieved by wet grinding with the help of pearl mills.

To prepare a stable aqueous suspension is not an easy task even for a technician. The colloid system is in a very sensitive equilibrium and can be influenced by several factors such as temperature, interactions among the elements of the system, etc. Physical and chemical characteristics of the suspendable substance (active ingredient) have a great significance and therefore there is no universal formulation recipe which could be applied for any active ingredient. Technicians generally accept it as a basic requirement that the substance to be formulated should be practically water insoluble, should have a relatively high melting, point and should be resistant to hydrolysis.

Beta-cypermethrin meets partly these requirements because its water solubility at 20° C. is 0.01 mg/liter and with addition of certain substances (e.g. maleinic acid, malonic acid, phthalic acid) its chemical stability can also be insured.

The difficulty had lain in its relatively low (60 to 65° C.) melting point which caused the failure of the early formulation trials. Although the temperature of the suspension during usual grinding, processes did not quite reach 60° C. (generally it was between 35 to 50° C.) the active ingredient partly still melted or recrystallized.

The reason for this phenomenon is complex but it can be explained partly by the liberation of local energy formed on collision and friction points of the grinding bodies (pearls), partly by the plastification (melting point decreasing) effect of surfactants.

It was our aim to find such auxiliary substances which eliminate the above mentioned disadvantageous effects have easy accessibility and are compatible with other components of the suspension system.

In the course of our experiments We found that certain water insoluble silicates such as kaolin if (ground together with beta-cypermethrin inhibit its melting and recrystallization, moreover decrease the tendency to setting which is characteristic of pyrethroid preparations in aqueous suspensions with low (2 to 5% by mass) active ingredient concentration.

In the course of our experiments we have found surprisingly that beta-cypermethrin is inclined to recrystallization if stored at higher temperature in spite of its extremely low water solubility (0.01 mg/l 20° C.). This phenomenon can be explained by increased water solubility of the active ingredient at higher temperature, which solubility can be further increased by the solubilizing effect of surface active substances. Growing particle size is an unfavorable phenomenon in the suspension because as a result of this the biological effectiveness and physical stability of the product may decrease. In the course of our formulation experiments we tried to inhibit the growth of the suspended particles and we found that this goal can be achieved by application of certain synthetic, amorph silicic acids (e.g,. Wessaion S).

As we mentioned earlier in order to insure chemical stability of beta-cypermethrin, that is to inhibit undesired epimerization, different organic acids are used. In the course of our experiments we were able to find such substances which chemically stabilize beta-cypermethrin and at the same time possess good dispersing and wetting effects both during grindings and application of the product. In addition they protect well the particles of the active ingredients and inorganic auxiliary materials against changes e.g. agglomeration during storage.

These surface active and physicochemical stabilizer compounds are ethoxylated polyaryl-phenol-phosphates or sulfates and from these ethoxylated tristyryl-phenol-phosphates proved to be very useful especially those that contain 16 moles of ethoxy groups.

Aqueous suspensions of pesticides according to our invention contain the following components:

- 0.1–20% by mass beta-cypermethrin
- 0–40% by mass other pesticide substances
- 1–10% by mass surface active substances in total and within this
- 1–5% by mass ethoxylated polyaryl-phenol-phosphate or sulfate
- 0.1–25% by mass mineral and/or synthetic silicates
- 0.1–1% by mass synthetic silicic acid and to make up to 100% by mass with other auxiliary material(s) and water as dispersant.

Under other active ingredients, compounds may be considered whose target of application and the time of application coincide with that of beta-cypermethrin, are compatible with other components of the formulation of the invention and can be formulated in stable aqueous suspensions. In a wider sense these active ingredients may be pesticides, growth regulators, adjuvants, repellents attractants and synergizing substances.

Beside the already mentioned ethoxylated polyarylphenol-phosphates and sulfates other dispersing and wetting substances may be used as surface active substances such as lignin sulfonates ethoxy-propoxy block copolymers, condensed aromatic sulfonic acids, ethoxylated alkyl phenols, aromatic alkyl sulfonic acids, ethoxylated fatty alcohols, etc.

As mineral silicates kaolinites and aluminum silicates may be used. Suitable thickeners are e.g. polysaccharides (e.g. xanthan-gum) and cellulose ethers. As antifreeze substances e.g. ethylene or propylene glycol may be used. Formaldehyde or 1,2-benzisothiazoline-3-on may be suitable conserving agents against microbial degradation of thickener polysaccharides. For example potassium hydroxide, sodium carbonate or triethanolamine can be used as organic or inorganic, bases. Useful antifoaming agents are silicon) emulsions. The compositions of the present invention are pesticides with excellent physical and chemical stability which can be sprayed diluted with water or undiluted, may be used as a seed coating substance alone or together with other treating agents and they can also be used in insect traps together with attractants or alone.

In the following examples we illustrate the composition and manufacturing processes of the present invention without limitation of our patent claim.

EXAMPLES

Example 1

Preparation of a pesticide formulation containing 5% by mass of active ingredient.

The formulation is prepared in two steps. First a more concentrated (15% by mass active ingredient) suspension is made which is diluted to 5% by mass by addition of auxiliary substances. 3 parts of ethoxylated tristyryl-phenol-phosphate dispersing agent and 0.6 parts of silicon defoamer are dissolved in 64.3 parts of water. To the solution 15 parts of beta-cypermethrin insecticide active ingredient, 15 parts of kaolin and 2.1 parts of synthetic silicic acid are added under vigorous agitation and the coarse suspension obtained is grinded in a pearl mill to average particle size of 2 $\mu$m. The fine suspension thus obtained is diluted three times of its mass by adding additional components according to the following: To 100 parts of the suspension 133.7 parts of water 6 parts of ethoxylated tristyryl-phenol-phosphate and 30 parts of triethanolamine 30 parts of glycol and 30 parts of 2% Xanthan-gum solution are added.

The following composition is obtained:

| | |
|---|---|
| beta-cypermethrin | 5.0% by mass |
| ethoxylated tristyryl-phenol-phosphate | 3.0% by mass |
| kaolin | 5.0% by mass |
| silicic acid | 0.7% by mass |
| propylene glycol | 10.0% by mass |
| xanthan gum | 0.2% by mass |
| triethanolamine | 0.1% by mass |
| water | 76.0% by mass |

The product is a suspension of grayish white color. Its density is 1.05 g/cm$^3$ at 20° C.

Example 2

The product prepared according to example 1 was stored at 45° C. for 1 month and for 1 year in a warehouse in the open without heating and its physico-chemical characteristics were measured. Results are listed in Table 1.

TABLE 1

| Storage conditions | Average particle size | Upper separation | Sediment | Active ingredient (%) | | |
|---|---|---|---|---|---|---|
| | | | | Total | cis(S) isomer | trans(S) isomer |
| Before storage | 1.2 $\mu$m | 0 | 0 | 4.97 | 1.98 | 2.99 |
| 2 weeks at 45° | 1.7 $\mu$m | 0 | 0 | 4.92 | 1.97 | 2.95 |
| 1 month at 45°C. | 1.7 $\mu$m | trace | 0 | 4.94 | 1.89 | 3.05 |
| I year in ware house | 1.9 $\mu$m | 0 | 0 | 4.99 | 1.97 | 3.02 |

Example 3

Biological efficacy on house-fly laboratory

Quantities of 0.5 ml tart solution made by serial dilution were spayed onto the bottom of Petri dishes (9 mm diameter) by using Potter-tower (Potter, C. Annals of Applied Biology, 39:1–78). After drying 10—10 2–4 day-old adult female house flies (Muscadomestica, WHO/SRS strain) were placed in the Petri dishes, which were then covered. The flies recovered within half an hour. Mortality was assessed after 24 hour-exposition on deposit.

Control treatments were done with tap water only. Tests were performed in three paralels and repeated at 2–5 occasions. LC$_{50}$ values were calculated from dose-mortality relationships by probit-analysis (Labsware, Probit analysis, CompuDrug, Budapest).

Results are listed in Table 2.

TABLE 2

| Formulation | Active ingredient | n[1] | Slope[2] | SE[3] | LV50[4] ppm | SE[5] |
|---|---|---|---|---|---|---|
| Chinmix 5 EC | beta-cypermethrin | 720 | 1.52 | 0.11 | 14.2 | 1.2 |
| Fendona 10 FW | alpha-cypermethrin | 540 | 1.31 | 0.12 | 12.2 | 1.3 |
| Chinmix 5 SC | beta-cypermethrin | 540 | 1.70 | 0.13 | 8.2 | 0.7 |

[1]Number of treated flies used to the calculation of LC50
[2]Slope of log-concentration and probit-mortality
[3]Standard error of the slope
[4]Equipotential concentration
[5]Standard error of LC50

Data of the Table show that the efficacy of Chinmix SC prepared according to example 1 is significantly higher than that of Chinmix 5 EC containing the same active ingredient or that of Fendona 10 FW containing alpha-cypermethrin.

Example 4: Biological efficacy on Colorado beetle in field test.

Comparative field tests of Chinmix SC prepared according to example 1 and standard Chinmix 5 EC formulations were done on Colorado beetle adults (Leptinotarsa decemlineata).

Treatments were carried out on the 4th of August using backpack spraying machine with 500 l spraying solution. Area: 100 m$^2$. Repetition 4 in each dose Efficacy was assessed at 1, 5, 9 days after treatment by counting living insects on 5×4 designated stems per lot. Efficacy was calculated by Henderson-Tilton formula.

Results are shown in Table 3.

| Formulation | Dose (l/ha) | % Efficacy (Henderson-Tilton) | | |
|---|---|---|---|---|
| | | Day 1 | Day 2 | Day 3 |
| Chinmix 5 EC | 0.35 | 48.5 | 68.6 | 38.0 |
| Chinmix 5 SC | 0.30 | 88.3 | 79.1 | 61.5 |

Results of the Table show that also a lower dose of Chinmix SC is significantly more effective on Colorado beetle imagos than that of the EC-formulation.

What we claim is:

1. An aqueous suspension comprising:
   0.1–20% by mass beta-cypermethrin;
   1–10% by mass surface active substances;
   1–5% by mass ethoxylated polyaryl-phenol-phosphate or sulfate,
   0.1–25% by mass mineral and/or synthetic silicates;
   0.1–1% by mass synthetic silicic acid; and
   up to 100% by mass auxiliary materials and water as dispersant.

2. The aqueous suspension according to claim 1, wherein said ethoxylated polyaryl-phenol-phosphate is ethoxylated tristyryl-phenol phosphate with 16 EO-units.

3. The aqueous suspension according to claim 1, wherein said silicate is kaolin.

4. The aqueous suspension according to claim 1, wherein said surface active substance is 1–5% by mass non-ionic surfactant.

5. A process for preparing an aqueous suspension according to claim 1, comprising
   grinding beta-cypermethrin together with mineral and/or synthetic silicates, ethoxylated polyaryl-phenol-phosphate or sulfate and synthetic silicic acid to form a suspension comprising beta-cypermethrin; and
   adding a surface active substance, auxiliary material, and water to the suspension comprising beta-cypermethrin wherein the amounts of beta-cypermethrin, surface active substance, ethoxylated polyaryl-phenol-phosphate or sulfate, mass mineral and/or synthetic silicates, synthetic silicic acid, auxiliary materials and water in the resultant aqueous suspension are sufficient to comprise 0.1–20% by mass beta-cypermethrin, 1–10% by mass surface active substance, 1–5% by mass ethoxylated polyaryl-phenol-phosphate or sulfate, 0.1–25% by mass mineral and/or synthetic silicates, 0.1–1% by mass synthetic silicic acid, and up to 100% by mass auxiliary materials and water.

6. The aqueous suspension according to claim 1, wherein said auxiliary material is 0.1–1% by mass thickener.

7. The aqueous suspension according to claim 6, wherein said thickener is xanthan gum.

8. The aqueous suspension according to claim 1, further comprising antifreeze.

9. The aqueous suspension according to claim 1, wherein said antifreeze is propylene glycol.

10. The aqueous suspension according to claim 1, further comprising a basic compound.

11. The aqueous suspension according to claim 10, wherein said basic compound is triethanolamine.

12. The aqueous suspension according to claim 1, further comprising 0.1–1% by mass antifoaming agent.

13. The aqueous suspension according to claim 12, wherein said antifoaming agent is a silicone emulsion.

14. The aqueous suspension according to claim 1, further comprising 0.01–1.0% by mass preserving substance.

15. The aqueous suspension according to claim 14, wherein said preserving substance is formaldehyde.

* * * * *